(12) United States Patent
Maxey et al.

(10) Patent No.: US 9,410,877 B2
(45) Date of Patent: Aug. 9, 2016

(54) DETERMINING WELLBORE FLUID PROPERTIES

(71) Applicant: Halliburton Energy Services, Inc., Houston, TX (US)

(72) Inventors: Jason Eric Maxey, Spring, TX (US); Xiangnan Ye, Cypress, TX (US); HsinChen Chung, Houston, TX (US); Narongsak Tonmukayakul, Spring, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 739 days.

(21) Appl. No.: 13/650,943

(22) Filed: Oct. 12, 2012

(65) Prior Publication Data

US 2014/0105446 A1    Apr. 17, 2014

(51) Int. Cl.
| | |
|---|---|
| *G01N 11/04* | (2006.01) |
| *G01N 11/06* | (2006.01) |
| *E21B 49/08* | (2006.01) |
| *G01N 33/28* | (2006.01) |
| G01N 11/00 | (2006.01) |
| G01N 9/32 | (2006.01) |

(52) U.S. Cl.
CPC ............... *G01N 11/04* (2013.01); *E21B 49/08* (2013.01); *G01N 33/2823* (2013.01); *G01N 9/32* (2013.01); *G01N 11/06* (2013.01); *G01N 2011/0026* (2013.01); *G01N 2291/02818* (2013.01); *G06T 2207/30108* (2013.01)

(58) Field of Classification Search
CPC .............................. G01N 11/06; G01N 11/04
See application file for complete search history.

(56) References Cited

U.S. PATENT DOCUMENTS

| | | | | |
|---|---|---|---|---|
| 3,699,804 A | * | 10/1972 | Gassmann et al. | 73/54.07 |
| 4,302,965 A | * | 12/1981 | Johnson et al. | 73/54.07 |
| 4,828,034 A | * | 5/1989 | Constien et al. | 166/308.4 |
| 5,327,778 A | * | 7/1994 | Park | 73/54.21 |
| 5,414,778 A | * | 5/1995 | Schwartz et al. | 382/142 |

(Continued)

FOREIGN PATENT DOCUMENTS

WO    WO 2013005185 A1 * 1/2013

OTHER PUBLICATIONS

Mobile Phone Enabled Pervasive Measurement of Liquid Viscosity by Yang Yang et al, pp. 1-5 2011.*

(Continued)

*Primary Examiner* — Akash Saxena
(74) *Attorney, Agent, or Firm* — Craig Roddy; Fish & Richardson P.C.

(57) ABSTRACT

Computer-implemented methods, software, and systems for determining a property of a wellbore fluid are disclosed. In some implementations, a computing system receives an image of a first sample of the wellbore fluid filling a conduit to a threshold volume of the conduit. The computing system determines a first time duration of the first sample of the wellbore fluid filling the conduit to the threshold volume of the conduit based on the image of the first sample. The computing system receives an image of a second sample of the wellbore fluid filling the conduit to the threshold volume of the conduit. The computing system determines a second time duration of the second sample of the wellbore fluid filling the conduit to the threshold volume of the conduit based on the image of the second sample. A property of the wellbore fluid is determined based on a difference between the first and second time durations.

11 Claims, 11 Drawing Sheets

(56) References Cited

U.S. PATENT DOCUMENTS

| | | | | |
|---|---|---|---|---|
| 6,152,888 | A * | 11/2000 | Kensey et al. | 600/573 |
| 6,412,337 | B1 * | 7/2002 | Arzate et al. | 73/54.09 |
| 6,428,488 | B1 * | 8/2002 | Kensey et al. | 600/573 |
| 6,564,618 | B2 * | 5/2003 | Shin et al. | 73/54.07 |
| 6,796,168 | B1 * | 9/2004 | Goldstein et al. | 73/54.01 |
| 7,188,515 | B2 * | 3/2007 | Burns et al. | 73/54.05 |
| 7,497,263 | B2 * | 3/2009 | Parris et al. | 166/308.5 |
| 7,673,507 | B2 * | 3/2010 | Walters et al. | 73/152.55 |
| 7,781,380 | B2 * | 8/2010 | Lin et al. | 507/211 |
| 8,424,368 | B2 * | 4/2013 | Tonmukayakul | G01N 11/02 73/54.01 |
| 8,739,876 | B2 * | 6/2014 | Saini et al. | 166/305.1 |
| 2002/0007664 | A1 * | 1/2002 | Shin et al. | 73/54.07 |
| 2002/0040196 | A1 * | 4/2002 | Kensey | A61B 5/02035 600/573 |
| 2006/0151172 | A1 * | 7/2006 | Hanes et al. | 166/300 |
| 2006/0166836 | A1 * | 7/2006 | Pena et al. | 507/211 |
| 2006/0166837 | A1 * | 7/2006 | Lin et al. | 507/211 |
| 2007/0056358 | A1 * | 3/2007 | Liu | 73/54.41 |
| 2009/0320568 | A1 * | 12/2009 | Desie et al. | 73/54.07 |
| 2010/0274504 | A1 * | 10/2010 | Takahashi et al. | 702/50 |
| 2011/0249266 | A1 * | 10/2011 | Kumar | 356/440 |
| 2012/0022807 | A1 * | 1/2012 | Weng et al. | 702/50 |
| 2012/0180553 | A1 * | 7/2012 | Henning et al. | 73/54.42 |
| 2012/0181033 | A1 * | 7/2012 | Saini et al. | 166/308.1 |
| 2014/0012507 | A1 * | 1/2014 | Trehan et al. | 702/12 |
| 2014/0216140 | A1 * | 8/2014 | Morhell et al. | 73/54.07 |
| 2014/0230527 | A1 * | 8/2014 | Lewis | G01N 11/06 73/54.06 |

OTHER PUBLICATIONS

Y. Yang et al., "Mobile Phone Enabled Pervasive Measurement of Liquid Viscosity" Appl. Rheol. vol. 21, Issue 6, 63890 (2011) (5 pages).

* cited by examiner

DETERMINING WELLBORE FLUID PROPERTIES

TECHNICAL BACKGROUND

This disclosure relates to determining wellbore fluid properties.

BACKGROUND

When preparing a wellbore fluid by mixing a polymer, such as guar gum, or clays, such as bentonite, into an aqueous fluid, a minimum mixing time is required to achieve full hydration, and thus the maximum viscosity of the fluid. Allowing the polymer or clay to fully hydrate is important for reaching the maximum stable viscosity for transport and application of the fluid downhole. Additionally, when the fluid is to be cross-linked, obtaining maximum hydration also maximizes the efficiency of the cross-linking and the rheological properties of the cross-linked fluid. Traditional oilfield viscosity measurements are carried out on instruments such as viscometers.

DETAILED DESCRIPTION

Figure 1:
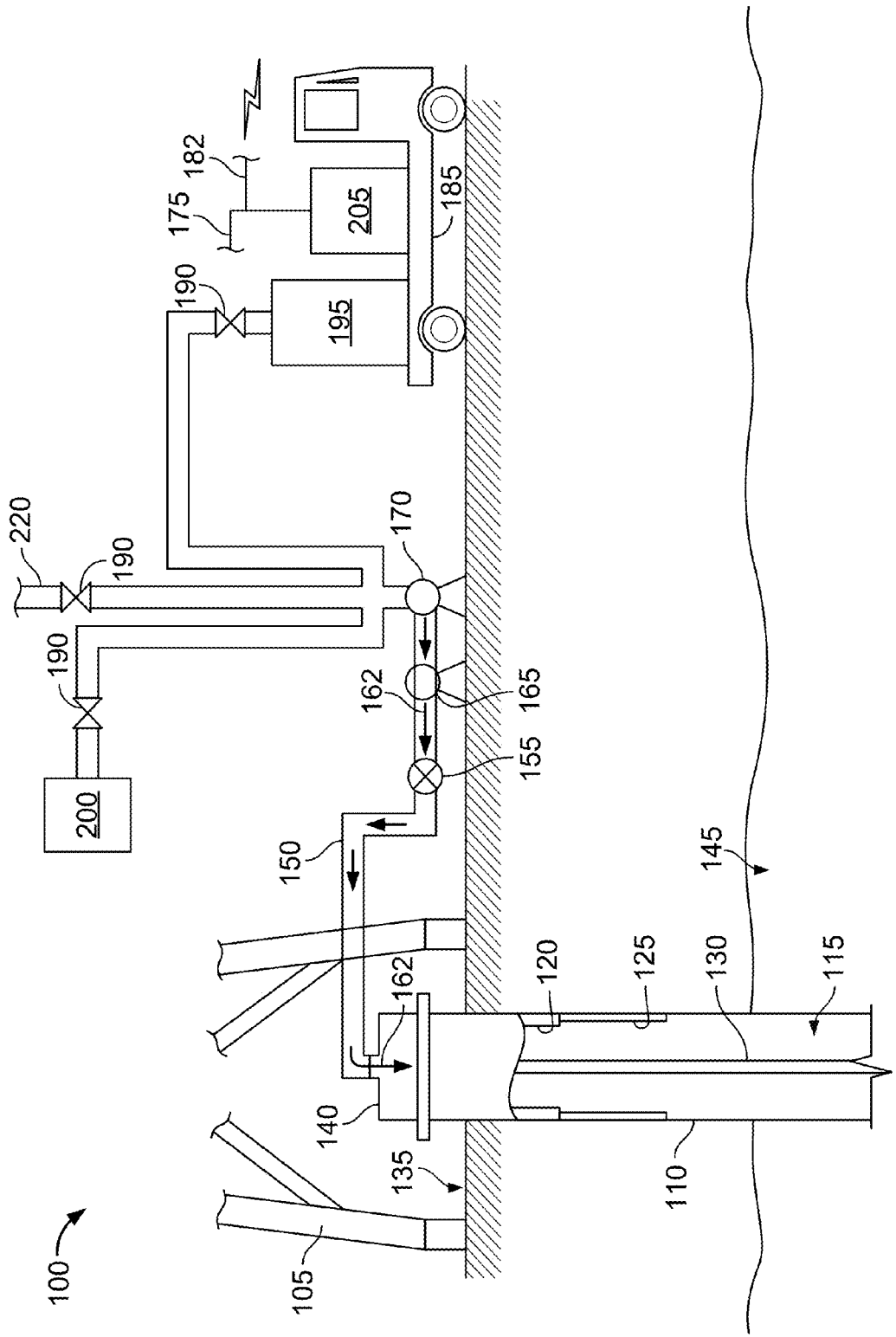
FIG. 1 illustrates an example implementation of at least a portion of a wellsite assembly in the context of a fracturing operation.

This disclosure generally describes computer-implemented methods, software, and systems for determining a property of a wellbore fluid. In some general implementations, a computing system receives an image of a first sample of the wellbore fluid filling a conduit to a threshold volume of the conduit. The computing system determines a first time duration of the first sample of the wellbore fluid filling the conduit to the threshold volume of the conduit based on the image of the first sample. The computing system receives an image of a second sample of the wellbore fluid filling the conduit to the threshold volume of the conduit. The computing system determines a second time duration of the second sample of the wellbore fluid filling the conduit to the threshold volume of the conduit based on the image of the second sample. A hydration percentage of the wellbore fluid is determined based on a difference between the first and second time durations.

In some general implementations, the computing system receives one or more images of a wellbore fluid sample that at least partially fills a vertically-oriented conduit. The computing system determines a steady-state level of the wellbore fluid sample within the conduit based on the one or more images. The computing system determines a time duration to fill the conduit with the wellbore fluid sample to the steady-state level based on the one or more images. The computing system determines the property of the wellbore fluid based at least in part on the steady-state level and the time duration.

In a specific aspect combinable with one or more of these general implementations, the wellbore fluid is a fracturing fluid, drilling fluid, completion fluid, or reservoir stimulation fluid.

In a specific aspect combinable with any of the previous aspects, the conduit is a capillary tube.

A specific aspect combinable with any of the previous aspects includes receiving, at the computing system, an image of a third sample of the wellbore fluid filling the conduit to the threshold volume of the conduit A specific aspect combinable with any of the previous aspects includes determining the property of the wellbore fluid based on a difference between the first, the second, and the third time durations.

In a specific aspect combinable with any of the previous aspects, the property includes a hydration percentage of the wellbore fluid.

In a specific aspect combinable with any of the previous aspects, the computing system comprises a smart phone or a tablet computing device and the steps of receiving and determining are performed at a wellsite by the smart phone or tablet computing device.

A specific aspect combinable with any of the previous aspects includes capturing the one or more images of the wellbore fluid with the smart phone or the tablet computer device at a wellsite.

A specific aspect combinable with any of the previous aspects includes preparing a visual representation of the property of the wellbore fluid to be displayed on a graphical user interface of the computing system.

A specific aspect combinable with any of the previous aspects includes determining a viscosity of the wellbore fluid.

A specific aspect combinable with any of the previous aspects includes determining a hydration percentage of the wellbore fluid based on the viscosity of the wellbore fluid.

In a specific aspect combinable with any of the previous aspects, the viscosity is determined at least in part on a density of the wellbore fluid, a dimension of the conduit, and the first or second time duration.

In a specific aspect combinable with any of the previous aspects, the viscosity is based on the equation: $\mu = (\rho \times g \times h_c \times r^2 \times t)/(8 \times L^2)$, where t is the viscosity, $\rho$ is a wellbore fluid density, g is gravitational acceleration, $h_c$ is a conduit head height of the fluid, r is a radius of the conduit, t is one of the first or second time durations, and L is a length of the conduit.

In a specific aspect combinable with any of the previous aspects, the steps of receiving and determining are performed at a wellsite.

A specific aspect combinable with any of the previous aspects includes determining a fill level of the first sample of the wellbore fluid in the conduit based on a determined pixel length in the image of the first sample that corresponds to the fill level.

A specific aspect combinable with any of the previous aspects includes comparing the determined pixel length to a threshold pixel length that corresponds to a threshold volume of the conduit.

A specific aspect combinable with any of the previous aspects includes determining the first time duration based on a difference between a start time that occurs when the first sample begins to fill the conduit and an end time that occurs when the determined pixel length is substantially equal to the threshold pixel length.

In a specific aspect combinable with any of the previous aspects, the image of the first sample comprises a plurality of video images of the first sample filling a horizontally-orientated conduit.

In a specific aspect combinable with any of the previous aspects, the wellbore fluid is a non-Newtonian fluid.

In a specific aspect combinable with any of the previous aspects, the viscosity is determined at least in part on a density of the wellbore fluid and a dimension of the conduit.

In a specific aspect combinable with any of the previous aspects, the viscosity is based on the equation: $\mu=[(\rho \times g \times r^2 \times t)/8] \times [(h_{ss}-h(t)/h^2(t))]$; where $\mu$ is the viscosity, $\rho$ is a density of the wellbore fluid, g is gravitational acceleration, h is a height of the conduit, r is a radius of the conduit, t is the time duration, $h_{ss}$ is the steady state level, and h(t) is a height of the wellbore fluid as a function of the time.

Further example implementations are disclosed herein. For instance, in one example implementation, a viscosity of a wellbore fluid is determined based on a known property (e.g., capillary head height, surface tension, or other appropriate property) of the wellbore fluid and a mean velocity of the wellbore fluid as it fills a horizontally-oriented (with respect to gravitational acceleration) conduit, such as a capillary tube.

Various implementations of a computing system according to the present disclosure may have one or more of the following features. For example, a minimal amount of equipment at a minimal cost is used to determine the properties of the wellbore fluid. Additionally, the equipment does not need an outside power source, thus the testing can be performed at multiple locations. The results of testing may also be available in real time as samples are analyzed.

The details of one or more implementations of the subject matter of this specification are set forth in the accompanying drawings and the description below. Other features, aspects, and advantages of the subject matter will become apparent from the description, the drawings, and the claims.

Other general implementations include corresponding computer systems, apparatus, and computer programs recorded on one or more computer storage devices, each configured to perform the actions of the methods. A system of one or more computers can be configured to perform operations to perform the actions. One or more computer programs can be configured to perform particular operations or actions by virtue of including instructions that, when executed by data processing apparatus, cause the apparatus to perform the actions.

FIG. 1 illustrates one implementation of at least a portion of a wellsite assembly 100 in the context of a fracturing operation. A wellbore 110 is formed from a terranean surface 135 to and/or through a subterranean zone 145. The illustrated wellsite assembly 100 includes a drilling rig 105; a tubing system 150 coupled to a fluid valve 155, a pump 165, a mixer 170, a liquid source 220; and a frac fluid truck 185 coupled to the tubing system 150. Although illustrated as onshore, the wellsite assembly 100 and/or wellbore 110 can alternatively be offshore or elsewhere. Further, although described in the context of a fracing operation, the wellsite assembly 100 may also illustrate another downhole operation that uses a fluid, such as a liquid, slurry, gel, or other fluid.

The wellbore 110, at least a portion of which is illustrated in FIG. 1, extends to and/or through one or more subterranean zones under the terranean surface 135, such as subterranean zone 145. Wellbore 110 may allow for production of one or more hydrocarbon fluids (e.g., oil, gas, a combination of oil and/or gas, or other fluid) from, for example, subterranean zone 145. The wellbore 110 is cased with one or more casings. As illustrated, the wellbore 110 includes a conductor casing 120, which extends from the terranean surface 135 shortly into the Earth. Other casing 125 is downhole of the conductor casing 120. Alternatively, some or all of the wellbore 110 can be provided without casing (e.g., open hole). Additionally, in some implementations, the wellbore 110 may deviate from vertical (e.g., a slant wellbore or horizontal wellbore) and/or be a multilateral wellbore.

A wellhead 140 is coupled to and substantially encloses the wellbore 110 at the terranean surface 135. For example, the wellhead 140 may be the surface termination of the wellbore 110 that incorporates and/or includes facilities for installing casing hangers during the well construction phase. The wellhead 140 may also incorporate one or more techniques for hanging tubing 130, installing one or more valves, spools and fittings to direct and control the flow of fluids into and/or from the wellbore 110, and installing surface flow-control facilities in preparation for the production phase of the wellsite assembly 110.

The tubing system 150 is coupled to the wellhead 140 and, as illustrated, provides a pathway through which one or more fluids, such as fluid 162, into the wellbore 110. In certain instances, the tubing system 150 is in fluid communication with the tubing 130 extending through the wellbore 110. The fluid 162, in the illustrated implementation of FIG. 1, is a fracing fluid introduced into the wellbore 110 to generate one or more fractures in the subterranean zone 145.

In the implementation of FIG. 1 illustrating a fracing completion operation, the tubing system 150 is used to introduce the fluid 162 into the wellbore 110 via one or more portions of conduit and one or more flow control devices, such as the control valve 155, the pump 165, the mixer 170, one or more valves 190 (e.g., control, isolation, or otherwise), the liquid source 220, and the truck 185. Generally, the pump 165, the mixer 170, the liquid source 220, and the truck 185 are used to mix and pump a fracing fluid (e.g., fluid 162) into the wellbore 110.

The well assembly 100 includes gel source 195 and solids source 200 (e.g., a proppant source). Either or both of the gel source 195 and solids source 200 could be provided on the truck 185. Although illustrated as a "truck," truck 185 may represent another vehicle-type (e.g., tractor-trailer or other vehicle) or a non-vehicle permanent or semi-permanent structure operable to transport and/or store the gel source 195 and/or solids source 200. Further, reference to truck 185 includes reference to multiple trucks and/or vehicles and/or multiple semi-permanent or permanent structures.

The gel from the gel source 195 is combined with a hydration fluid, such as water and/or another liquid from the liquid source 220, and proppant from the solids source 200 in the mixer 170. Proppant, generally, may be particles mixed with fracturing fluid (such as the mixed gel source 195 and liquid source 220) to hold fractures open after a hydraulic fracturing treatment.

Notably, although the concepts described herein are discussed in connection with a fracturing operation, they could be applied to other types of operations. For example, the wellsite assembly could be that of a cementing operation where a cementing mixture (Portland cement, polymer resin, and/or other cementing mixture) may be injected into wellbore 110 to anchor a casing, such as conductor casing 120 and/or surface casing 125, within the wellbore 110. In this situation, the fluid 162 could be the cementing mixture. In another example, the wellsite assembly could be that of a drilling operation, including a managed pressure drilling operation. In another example, the wellsite assembly could be that of a stimulation operation, including an acid treatment. Still other examples exist.

Figure 2:
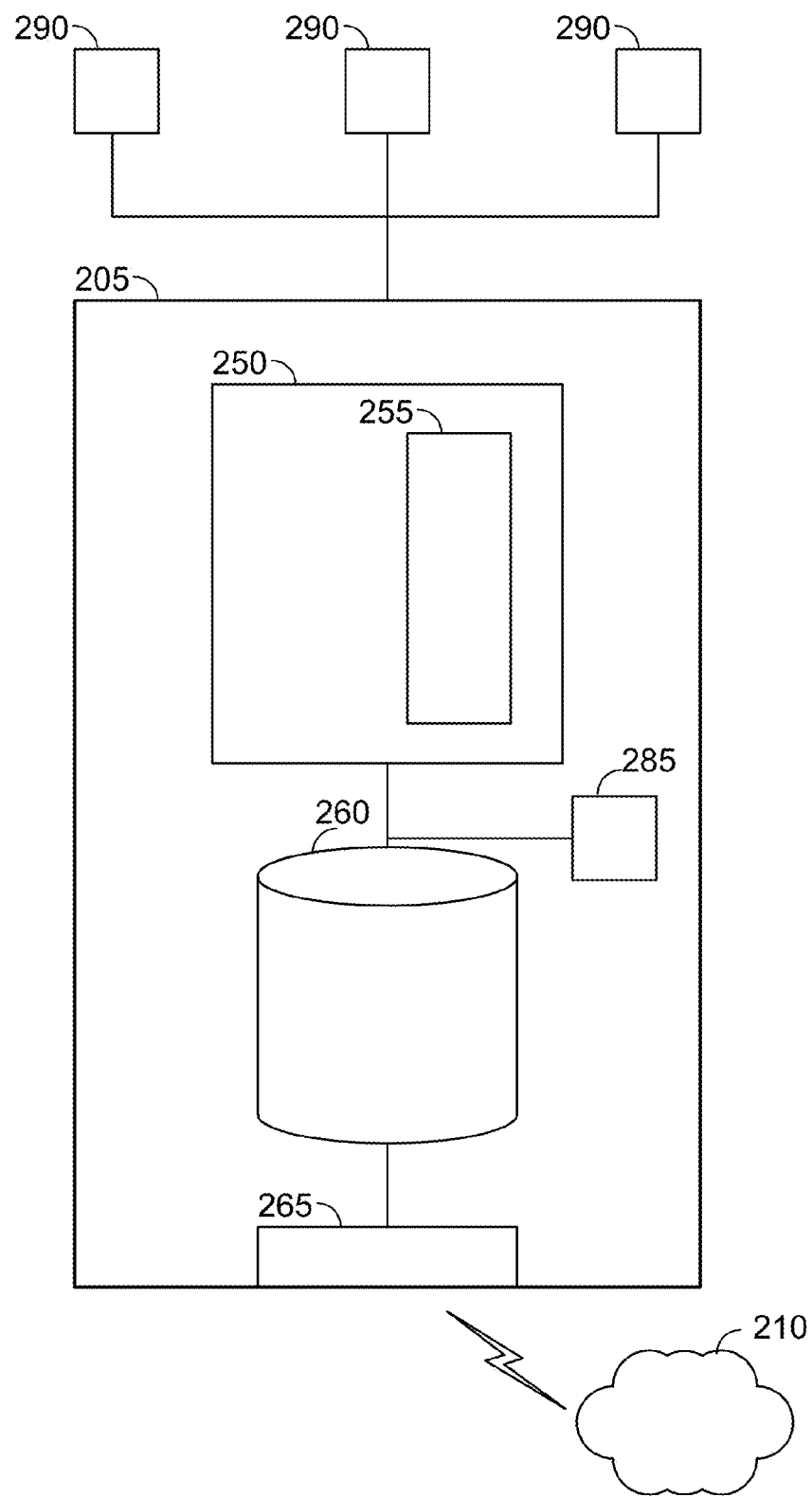
FIG. 2 illustrates an example implementation of a computer utilized at or remote from the wellsite assembly.

FIG. 2 illustrates one implementation of the computer 205 utilized at or remote from the wellsite assembly 100. Although illustrated as located on the truck 185, for example, the computer 205 may be physically located at another location, such as remote from the wellsite assembly 100 or at the wellsite but remote from the truck 185 (e.g., at a wellsite trailer or otherwise). The illustrated computer 205 includes a processor 250 executing a fluid property engine 255, a memory 260, a network interface 265, and one or more input/output peripherals 290. In certain implementations, the computer 205 may be the computer used in connection with one or more operations of the well assembly 100 (e.g., data collection from the fracturing operation, controlling some or all of the gel, solids and liquid mixing, controlling some or all of the fracturing operations and/or other operations).

At a high level, the fluid property engine 255 is executed by the processor 250 to determine one or more properties of the fluid 162. In some examples, the property can include a viscosity, a hydration percentage, both, or other property of the fluid 162. More specifically, the fluid property engine 255 is any application, program, module, process, or other software that receives one or more images (e.g., a video) representative of the fluid 162 filling a conduit, and determines one or properties (e.g., the viscosity, the hydration percentage) representative of the fluid 162 from the one or more images. Regardless of the particular implementation, "software" may include software, firmware, wired or programmed hardware, or any combination thereof as appropriate. Indeed, fluid measuring module 255 may be written or described in any appropriate computer language including C, C++, Java, Visual Basic, assembler, Perl, any suitable version of 4GL, as well as others. It will be understood that while the fluid property engine 255 is illustrated in FIG. 2 as a single module, the fluid property engine 255 may include numerous other sub-modules or may instead be a single multi-tasked module that implements the various features and functionality through various objects, methods, or other processes. Further, while illustrated as internal to computer 205, one or more processes associated with the fluid property engine 255 may be stored, referenced, or executed remotely. For example, a portion of the fluid property engine 255 may be a web service that is remotely called, while another portion of the fluid property engine 255 may be an interface object bundled for processing at a remote client. Moreover, the fluid property engine 255 may be a child or sub-module of another software module or enterprise application (not illustrated) without departing from the scope of this disclosure.

Processor 250 is, for example, a central processing unit (CPU), a blade, an application specific integrated circuit (ASIC), or a field-programmable gate array (FPGA). Although FIG. 2 illustrates a single processor 250 in computer 205, multiple processors 250 may be used according to particular needs and reference to processor 250 is meant to include multiple processors 250 where applicable. In the illustrated implementation, processor 250 executes the fluid property engine 255 as well as other modules as necessary. For example, the processor 250 may execute software that manages or otherwise controls the operation of the truck 185 during a completion (e.g., fracing or otherwise) operation.

Memory 260 is communicably coupled to the processor 250 and may include any memory or database module and may take the form of volatile or non-volatile memory including, without limitation, magnetic media, optical media, random access memory (RAM), read-only memory (ROM), removable media, or any other suitable local or remote memory component. Memory 120 may also include any other appropriate data such as VPN applications or services, firewall policies, a security or access log, print or other reporting files, HTML files or templates, data classes or object interfaces, child software applications or sub-systems, and others.

Interface 265 facilitates communication between computer 205 and other devices. As illustrated, the computer 205 may communicate with a remote monitoring location over network 210. Generally, interface 265 comprises logic encoded in software and/or hardware in a suitable combination and operable to communicate with network 210. More specifically, interface 265 may comprise software supporting one or more communications protocols associated with communications network 210 or hardware operable to communicate physical signals.

Network 210 facilitates wireless or wired communication between computer 205 and any other local or remote computer. Network 210 may be all or a portion of an enterprise or secured network. While illustrated as a single or continuous network, network 210 may be logically divided into various sub-nets or virtual networks without departing from the scope of this disclosure. Network 210 may communicate, for example, Internet Protocol (IP) packets, Frame Relay frames, Asynchronous Transfer Mode (ATM) cells, voice, video, data, and other suitable information between network addresses. Network 210 may include one or more local area networks (LANs), radio access networks (RANs), metropolitan area networks (MANs), wide area networks (WANs), all or a portion of the global computer network known as the Internet, and/or any other communication system or systems at one or more locations.

One or more peripheral devices 290 may be communicably coupled to and/or integral with the computer 205. For example, peripheral devices 290 may be one or more display devices (e.g., LCD, CRT, other display device); one or more data input devices (e.g., keyboard, mouse, light pin, or otherwise); one or more data storage devices (e.g., CD-ROM, DVD, flash memory, or otherwise) or other peripheral devices.

Figure 3:
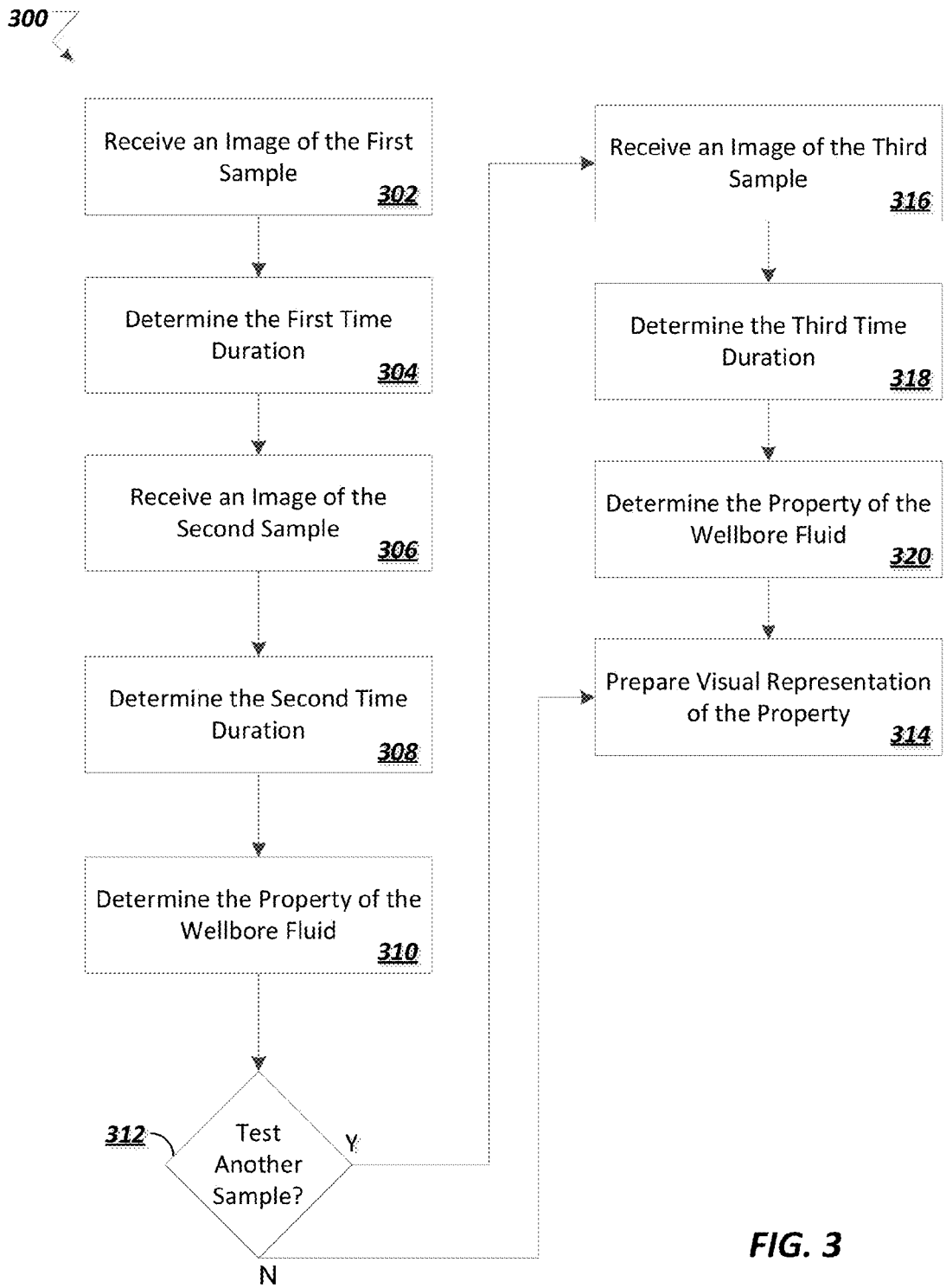
FIG. 3 illustrates an example method for determining a property of a wellbore fluid.

FIG. 3 is a flow chart 300 for determining a property of a wellbore fluid. For clarity of presentation, the description that follows generally describes method 300 in the context of FIGS. 1 and 2. However, it will be understood that method 300 may be performed, for example, by any other suitable system, environment, software, and hardware, or a combination of systems, environments, software, and hardware as appropriate.

Figure 4A:
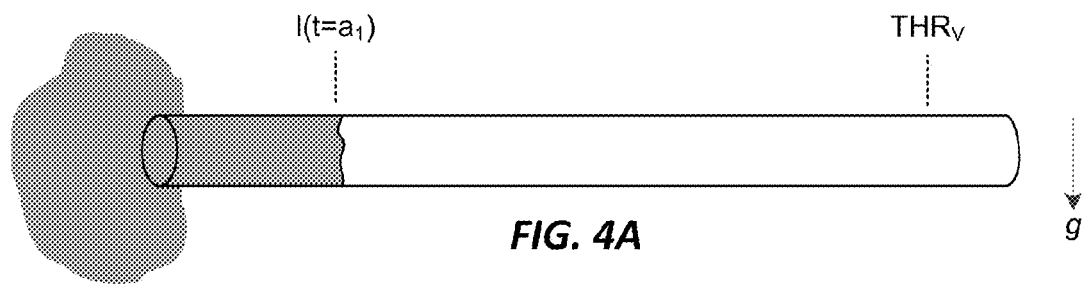
FIGS. 4A-4D and 5A-5D illustrate example implementations of a wellbore fluid filling a conduit.
Figure 4B:
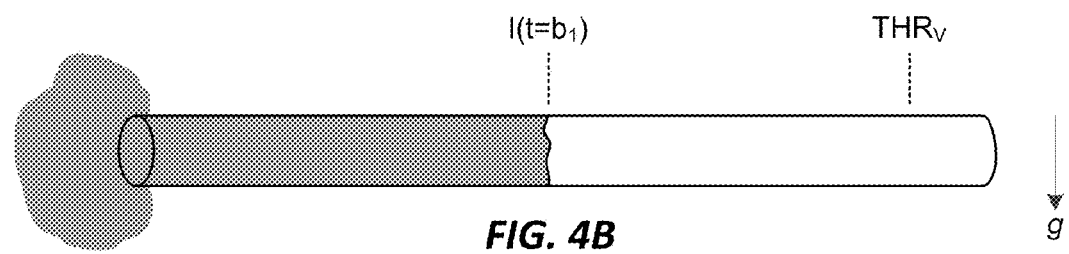
Figure 4C:
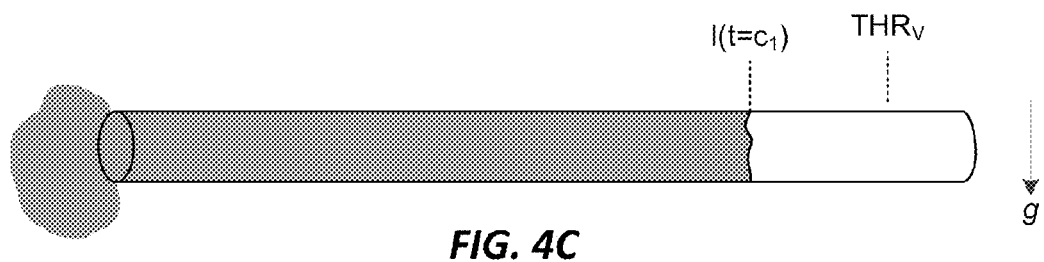
Figure 4D:
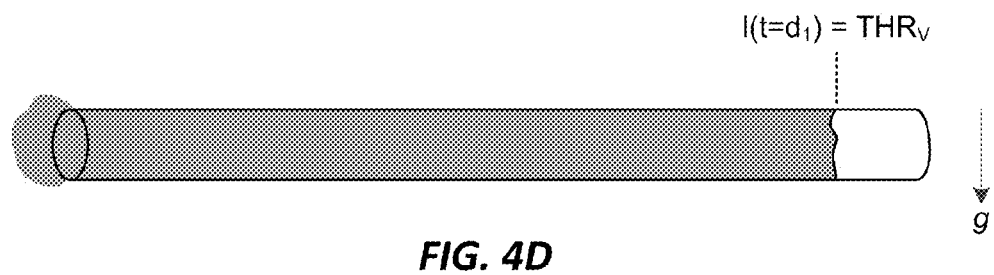

In step 302, a computing system receives an image of a first sample of a wellbore fluid filling a conduit to a threshold volume of the conduit. For example, the computer 205, and specifically the fluid property engine 255, receives an image of a first sample of a wellbore fluid filling a conduit to the threshold volume $THR_V$ of a conduit. As shown in FIGS. 4A-4D, a wellbore fluid 402 (e.g., fluid 162) fills a conduit 404. Specifically, the conduit 404 is positioned adjacent a "pool" of the wellbore fluid 402 (e.g., the conduct 404 is positioned to touch or be in contact with a "puddle" of the wellbore fluid 402). The wellbore fluid 402 fills the conduit 404, as shown in FIGS. 4A-4C, including filling the conduit 404 to the threshold volume $THR_V$ of the conduit 404, as shown in FIG. 4D. In some examples, each of the FIGS. 4A-4D can correspond or be associated with the image of the first sample of the wellbore fluid 402 filling the conduit 404.

For example, FIG. 4D can represent the first image of the wellbore fluid 402 filling the conduit 404 to the threshold volume $THR_V$ of the conduit 404.

In some examples, the wellbore fluid 402 fills the conduit 404 greater than the threshold volume $THR_V$. In some examples, the wellbore fluid 402 fills the conduit 404 via capillary action. In some examples, the threshold volume $THR_V$ is based on one or more properties (e.g., physical) of the conduit 404 (e.g., one or more dimensions of the conduit 404). In some examples, the threshold volume $THR_V$ is based on one or more properties of the wellbore fluid 402. Specifically, in some examples, the threshold volume $THR_V$ is based one or more properties of the wellbore fluid 402 when the wellbore fluid 402 fills the conduit 402 to the threshold volume $THR_V$.

In some implementations, the computer 205 provides, obtains, or enables access to, the image of the first sample of the wellbore fluid, as mentioned above. For example, the computer 205 can be or include a mobile computing device such as a smart phone or a tablet computing device. The computer 205, in the illustrated embodiment, includes or is communicably coupled with an image capturing device 285 (e.g., a camera) or have access to the image capturing device 285. For example, the mobile computing device can include an associated camera (e.g., single image camera or multiple (video) image camera). The camera can obtain the image(s) of the sample of the wellbore fluid 402 filling the conduit 404, as shown in FIGS. 4A-4D. In some examples, the image of the first sample of the wellbore fluid 402 filling the conduit 404 can include multiple (e.g., two or more) images of the first sample of the wellbore fluid 402 filling the conduit 404 (e.g., a sequence of multiple still images, or a video).

In some implementations, the conduit 404 is horizontally-orientated (e.g., horizontally-orientated with respect to gravity g). In some implementations, the multiple images of the first sample of the wellbore fluid 402 includes the multiple images of the first sample of the wellbore fluid 402 filling the horizontally-orientated conduit 404.

In some examples, the wellbore fluid 402 is a fracturing fluid (e.g., the fluid 162). In some examples, the conduit is a capillary tube. In some examples, the wellbore fluid 402 is a non-Newtonian fluid. In some examples, the wellbore fluid is a Newtonian fluid.

In step 304, the computing system determines a first time duration of the first sample of the wellbore fluid filling the conduit to the threshold volume of the conduit based on the image of the first sample. For example, the computer 205, and specifically the fluid property engine 255, determines the first time duration. As shown in FIGS. 4A-4D, the wellbore fluid 402 fills the conduit 404 over a time (e.g., a first time). Specifically, each of FIGS. 4A-4D depicts the wellbore fluid 402 filling the conduit 404 to certain lengths at specific times such that the length of the wellbore fluid 402 filling the conduit 404 is a function of (or based on) the time. For example, FIG. 4A depicts the wellbore fluid 402 filling the conduit 404 to a length l(t=a1) at a time a1; FIG. 4B depicts the wellbore fluid 402 filling the conduit 404 to a length l(t=b1) at a time b1; FIG. 4C depicts the wellbore fluid 402 filling the conduit 404 to a length l(t=c1) at a time c1; and FIG. 4D depicts the wellbore fluid 402 filling the conduit 404 to a length l(t=d1) at a time d1. Additionally, at time t=d1, the length of the wellbore fluid 402 filling the conduit 404 is equal to (or greater than) the threshold volume $THR_V$.

Thus, the fluid property engine 255 determines the time duration for the wellbore fluid 402 to fill the conduit 404 to the threshold volume $THR_V$ based on the image of the first sample. For example, the fluid property engine 255 determines the time d1 such that the length of the wellbore fluid 402 fills the conduit 402 to the threshold volume $THR_V$, and more specifically, the time d1 such that the length of the wellbore fluid 402 is equal to (or greater than) the threshold volume $THR_V$ (e.g., h(t=d1)=$THR_V$).

Figure 5A:
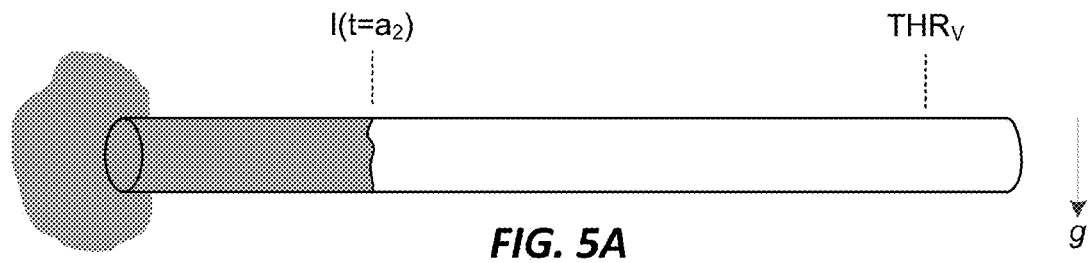
Figure 5B:
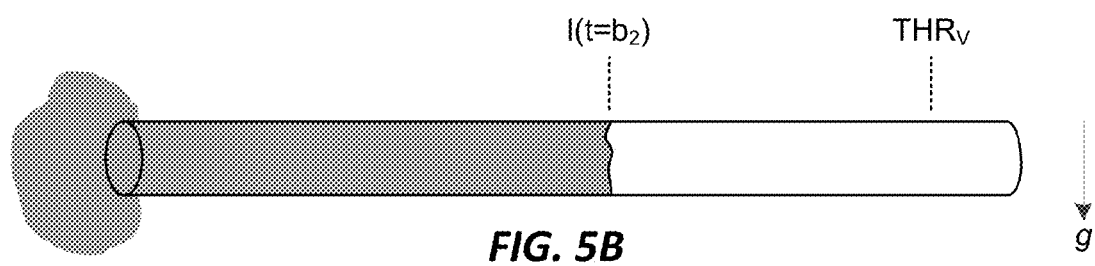
Figure 5C:
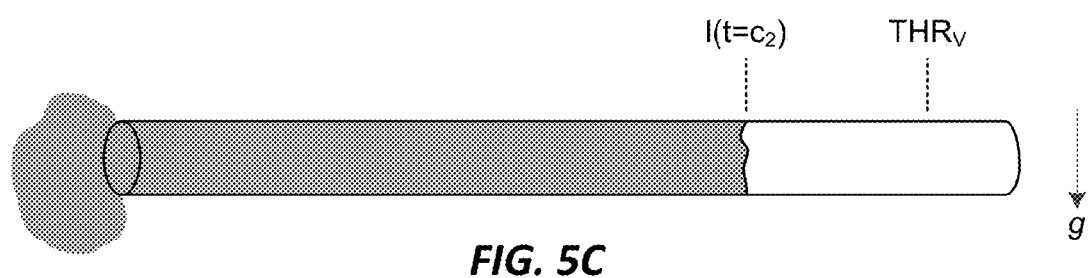
Figure 5D:
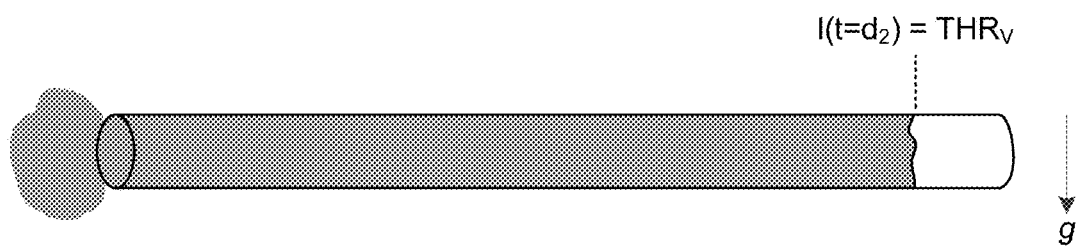

In step 306, the computing system receives an image of a second sample of the wellbore fluid filling the conduit to the threshold volume of the conduit. For example, the computer 205, and specifically the fluid property engine 255, receives an image of a second sample of the wellbore fluid 402 filling the conduit 404 to the threshold volume $THR_V$ of the conduit 404. As shown in FIGS. 5A-5C, the wellbore fluid 402 fills the conduit 404, including filling the conduit 404 to the threshold volume $THR_V$ of the conduit 404, as shown in FIG. 5D. In some examples, each of the FIGS. 5A-5D can correspond or be associated with the second image of the wellbore fluid 402 filling the conduit 404. For example, FIG. 5D can represent the second image of the wellbore fluid 402 filling the conduit 404 to the threshold volume $THR_V$ of the conduit 404.

In step 308, the computing system determines a second time duration of the second sample of the wellbore fluid filling the conduit to the threshold volume of the conduit based on the image of the second sample. For example, the computer 205, and specifically the fluid property engine 255, determines the second time duration. As shown in FIGS. 5A-5D, the wellbore fluid 402 fills the conduit 404 over a time (e.g., a second time). Specifically, each of FIGS. 5A-5D depicts the wellbore fluid 402 filling the conduit 404 to certain lengths at specific times, such that the length of the wellbore fluid 402 filling the conduit 404 is a function of (or based on) the time. For example, FIG. 5A depicts the wellbore fluid 402 filling the conduit 404 to a length l(t=a2) at a time a2; FIG. 5B depicts the wellbore fluid 402 filling the conduit 404 to a length l(b2=x) at a time b2; FIG. 5C depicts the wellbore fluid 402 filling the conduit 404 to a length l(t=c2) at a time c2; and FIG. 5D depicts the wellbore fluid 402 filling the conduit 404 to a length l(t=d2) at a time d2. Additionally, at time t=d2, the length of the wellbore fluid 402 filling the conduit 404 is equal to the threshold volume $THR_V$.

Thus, the fluid property engine 255 determines the time duration for the wellbore fluid 402 to fill the conduit 404 to the threshold volume $THR_V$ based on the image of the second sample. For example, the fluid property engine 255 determines the time d2 such that the length of the wellbore fluid 402 fills the conduit 402 to the threshold volume $THR_V$, and specifically, the time d2 such that the length of the wellbore fluid 402 is equal to (or greater than) the threshold volume $THR_V$ (e.g., h(t=d2)=$THR_V$).

In step 310, the computing system determines a property of the wellbore fluid based on a difference between the first and the second time durations. For example, the computer 205, and specifically the fluid property engine 255, determines a property of the wellbore fluid 402 based on the difference between the first time duration (e.g., t=d1) and the second time direction (e.g., t=d2). Specifically, the fluid property engine 255 compares the first time duration and the second time duration to determine the difference (e.g., variation) between the time for the wellbore fluid 402 to fill the conduit 404 to the threshold volume $THR_V$ (e.g., a difference between times d1 and d2). The fluid property engine 255 can identify whether the difference in time (e.g. variation) for the wellbore fluid 402 to fill the conduit 404 is within a predetermined tolerance (e.g., 1-3%). In some examples, the predetermined tolerance is based on one or more properties (e.g., physical) of the conduit 404 (e.g., one or more dimensions of the conduit 404). In some examples, the tolerance is based on one or more properties of the wellbore fluid 402. Furthermore, when the fluid property engine 255 identifies that the difference in time for the wellbore fluid 402 to fill the conduit 404 is within a predetermined tolerance, the time for the wellbore fluid 402 to fill the conduit 404 is considered to be in a steady-state condition.

In some examples, the property includes a hydration percentage of the wellbore fluid 402. In some examples, the property includes a viscosity of the wellbore fluid 402.

In step 312, it is determined whether a third sample of the wellbore fluid filling the conduit is to be tested. For example, the computer 205, and specifically the fluid property engine 255, determines whether the third sample of the wellbore fluid 402 filling the conduit 404 is to be tested. Specifically, the fluid property engine 255 determines whether the difference in time (e.g. variation) for the wellbore fluid 402 to fill the conduit 404 is within the predetermined tolerance based on the first time duration and the second time duration.

In step 314, based on determining that the difference in time (e.g. variation) for the wellbore fluid 402 to fill the conduit 404 is within a predetermined tolerance based on the first time duration and the second time duration, a visual representation of the property of the wellbore fluid to be displayed on a graphical user interface of the computing system 205 is prepared. For example, the computer 205 prepares a visual representation of the property (e.g., graphical data or text based data) to be displayed on a graphical user interface of the computer 205. Specifically, the computer 205 can prepare the visual representation for display on a display device (e.g., a display of a smart phone or a tablet computing device) of the computer 205 (e.g., one of the peripheral devices 290).

In step 316, based on determining that the difference in time (e.g. variation) for the wellbore fluid 402 to fill the conduit 404 is not within the predetermined tolerance based on the first time duration and the second time duration, the computing system receives an image of a third sample of a wellbore fluid filling the conduit to a threshold volume of the conduit. For example, the computer 205, and specifically the fluid property engine 255, receives an image of a third sample of a wellbore fluid 402 filling the conduit 404 to the threshold volume $THR_V$ of the conduit 404. Analogous to that shown in FIGS. 4A-4D and FIGS. 5A-5D, the wellbore fluid 402 fills the conduit 404, including filling the conduit 404 to the threshold volume $THR_V$ of the conduit 404.

In step 318, the computing system determines a third time duration of the third sample of the wellbore fluid filling the conduit to the threshold volume of the conduit based on the image of the third sample. For example, the computer 205, and specifically the fluid property engine 255, determines the third time duration. Analogous to that shown in FIGS. 4A-4D and FIGS. 5A-5D, the wellbore fluid 402 fills the conduit 404 over a time (e.g., a third time), and particularly, the wellbore fluid 402 fills the conduit 404 to a height h(t=d3) at a time d3. Additionally, at time t=d3, the length of the wellbore fluid 402 filling the conduit 404 is equal to (or greater than) the threshold volume $THR_V$.

Thus, the fluid property engine 255 determines the time duration for the wellbore fluid 402 to fill the conduit 404 to the threshold volume $THR_V$, based on the image of the third sample. For example, the fluid property engine 255 determines the time d3 such that the length of the wellbore fluid 402 fills the conduit 402 to the threshold volume $THR_V$, and specifically, the time d3 such that the length of the wellbore fluid 402 is equal to the threshold volume $THR_V$ (e.g., l(t=d3) =$THR_V$).

In step 320, the computing system determines the property of the wellbore fluid based on a difference between the first time duration, the second time duration, and the third time duration. For example, the computer 205, and specifically the fluid property engine 255, determines the property of the wellbore fluid 402 based on the difference between the first time duration (e.g., t=d1), the second time duration (e.g., t=d2), and the third time duration (e.g., t=d3). Specifically, the fluid property engine 255 compares the first time duration, the second time duration, and the third time duration to determine the difference (e.g., variation) between the time for the wellbore fluid 402 to fill the conduit 404 to the threshold volume $THR_V$ (e.g., a difference between times d1, d2, and d3). The fluid property engine 255 can identify whether the difference in time (e.g. variation) for the wellbore fluid 402 to fill the conduit 404 is within a predetermined tolerance (e.g., 1-3%). When the fluid property engine 255 identifies that the difference in time for the wellbore fluid 402 to fill the conduit 404 is within a predetermined tolerance, the time for the for the wellbore fluid 402 to fill the conduit 404 is considered to be in a steady-state condition.

In some implementations, the steps of receiving the images and determining the time durations are performed at a wellsite (e.g., proximate wellsite assembly 100).

Figure 6:
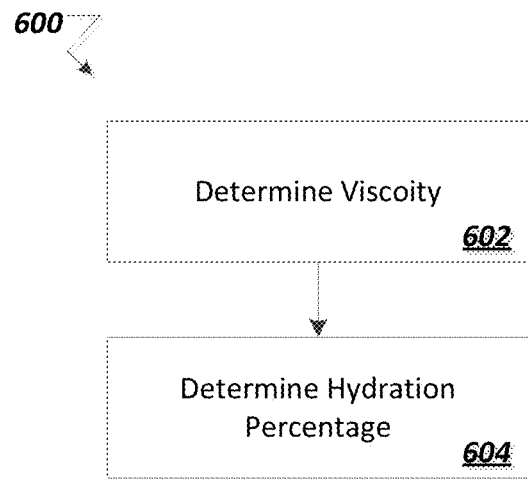
FIG. 6 illustrates an example method for determining a property of a wellbore fluid.

FIG. 6 is a flow chart 600 for determining a property of a wellbore fluid. For clarity of presentation, the description that follows generally describes method 600 in the context of FIGS. 1 and 2. However, it will be understood that method 300 may be performed, for example, by any other suitable system, environment, software, and hardware, or a combination of systems, environments, software, and hardware as appropriate.

In step 602, a viscosity of a wellbore fluid is determined. For example, the computer 205, and specifically the fluid property engine 255, determines the viscosity of the wellbore fluid 402. In some examples, determining the viscosity of the wellbore fluid 402 is based on determining one or more of the first time duration, the second time duration, and the third time durations. In some examples, determining the viscosity of the wellbore fluid 402 is based on determining the difference between one or more of the first time duration, the second time duration, and the third time durations.

In some implementations, the viscosity of the wellbore fluid 402 is determined in at least part on a density of the wellbore fluid, a dimension of the conduit, and the first or the second time duration. For example, the computer 205, and specifically the fluid property engine 255, determines the viscosity of the wellbore fluid based on at least the density of the wellbore fluid 402, a dimension of the conduit 404, and the first time duration, the second time duration, or both. In some examples, the dimension of the conduit 404 can include one or more of a height of the conduit 404, a radius of the conduit 404, and a length of the conduit. In some examples, the viscosity of the wellbore fluid 402 is further based on at least the third time duration.

In some implementations, the viscosity of the wellbore fluid 402 is based on the equation:

$$\mu = \frac{\rho g h_c r^2 t}{8L^2}$$

where μ is the viscosity of the wellbore fluid 402, ρ is a density of the wellbore fluid 402, g is gravitational acceleration, $h_c$ is a capillary head height of the fluid 402, r is a radius of the conduit 402, t is one of the first or second time durations, and L is a length of the conduit 402.

In step 604, a hydration percentage of the wellbore fluid is determined that is based on the viscosity of the wellbore fluid. For example, the computer 205, and specifically the fluid property engine 255, determines the hydration percentage of the wellbore fluid 402 based on the viscosity of the wellbore fluid 402. In some examples, the hydration percentage of the wellbore fluid 402 is correlated (directly) with a hydration index of the wellbore fluid 402.

Figure 7:
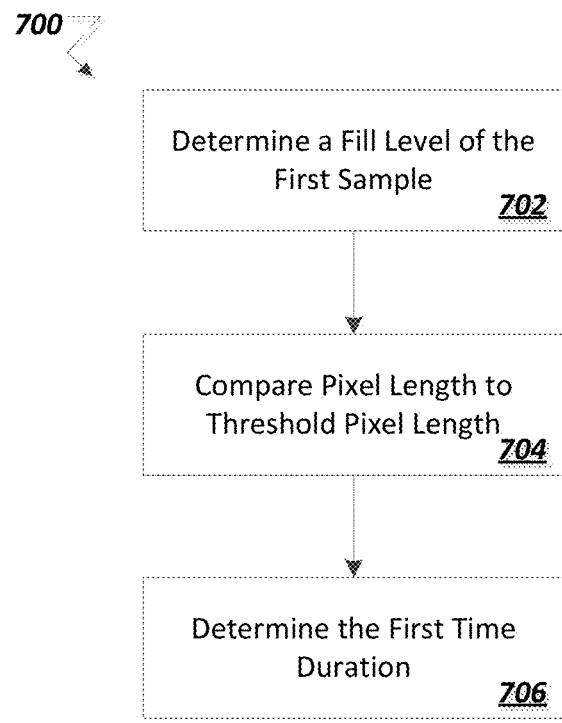
FIG. 7 illustrates an example method for determining fill-times of a conduit by a fluid.

FIG. 7 is a flow chart 300 for determining fill-times of a conduit by a fluid. For clarity of presentation, the description that follows generally describes method 700 in the context of FIGS. 1 and 2. However, it will be understood that method 300 may be performed, for example, by any other suitable system, environment, software, and hardware, or a combination of systems, environments, software, and hardware as appropriate.

In step 702, a fill level of the first sample of the wellbore fluid in the conduit is determined based on a determined pixel length in the image of the first sample that corresponds to the fill level. For example, the computer 205, and specifically the fluid property engine 255, determines the fill of the first sample of the wellbore fluid 402 based on determining a pixel length in the image of the first sample that corresponds to the fill level (e.g., FIGS. 4A-4D). Specifically, the fluid property engine 255 analyzes the first image (e.g., one of FIGS. 4A-4D) to determine a pixel length of the wellbore fluid 402 within the conduit 404 that corresponds to the fill level of the wellbore fluid 402 within the conduit 404. The pixel length is the number of pixels of the first image (one of FIGS. 4A-4D) corresponding to the fill length of the wellbore fluid 402 within the conduit 404 for any specific time (e.g., l(t=d1)). For example, a number of pixels can correspond to an actual length (e.g., 5 pixels of an image can correspond to 1 inch).

In step 704, the determined pixel length is compared to a threshold pixel length that corresponds to a threshold volume of the conduit. For example, the computer 205, and specifically the fluid property engine 255, compares the determined pixel length (of the fill level of the wellbore fluid 402 within the conduit 404) to a threshold pixel length THRPL. In some examples, the threshold pixel length THRPL corresponds to the threshold volume $THR_V$. For example, the threshold volume $THR_V$ corresponds to a number of pixels of the first image of the wellbore fluid 402 filling the conduit 404.

In step 706, the first time duration is determined based on a difference between a start time that occurs when the first sample begins to fill the conduit and an end time that occurs when the determined pixel length is substantially equal to the threshold pixel length. For example, the computer 205, and specifically the fluid property engine 255, determines the first time duration based on a difference between a start time (e.g., time a1) when the first sample of the wellbore fluid 402 fills the conduit 404 and an end time (e.g., time d1) when the determined pixel length is substantially equal to the threshold pixel length THRPL (e.g., when the wellbore fluid 402 fills the conduit 404 to the threshold volume $THR_V$).

Figure 8:
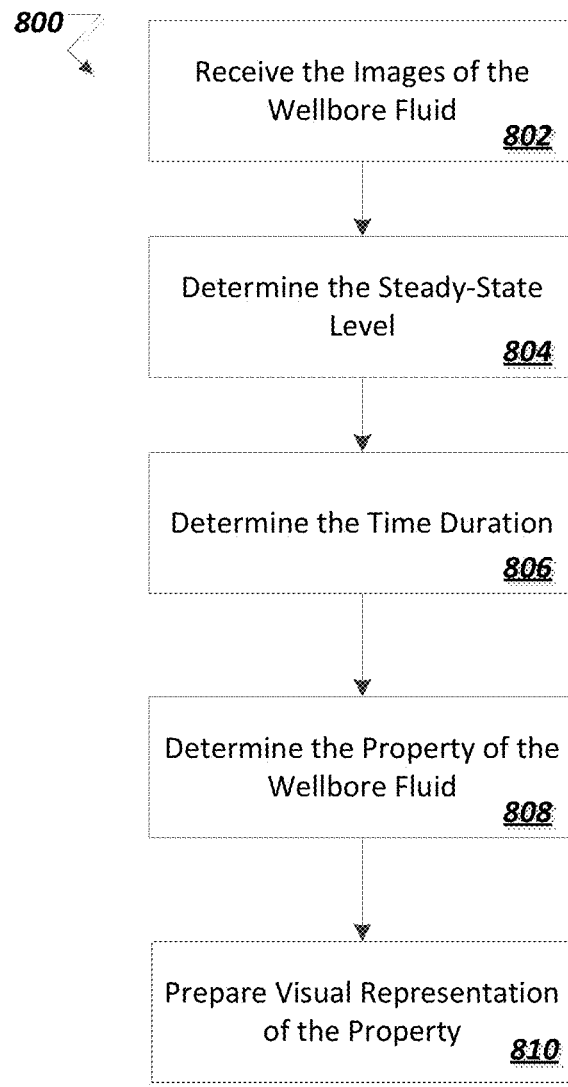
FIG. 8 illustrates an example method for determining a property of a wellbore fluid.

FIG. 8 is a flow chart 800 for determining a property of a wellbore fluid. For clarity of presentation, the description that follows generally describes method 800 in the context of FIGS. 1 and 2. However, it will be understood that method 300 may be performed, for example, by any other suitable system, environment, software, and hardware, or a combination of systems, environments, software, and hardware as appropriate.

Figure 9:
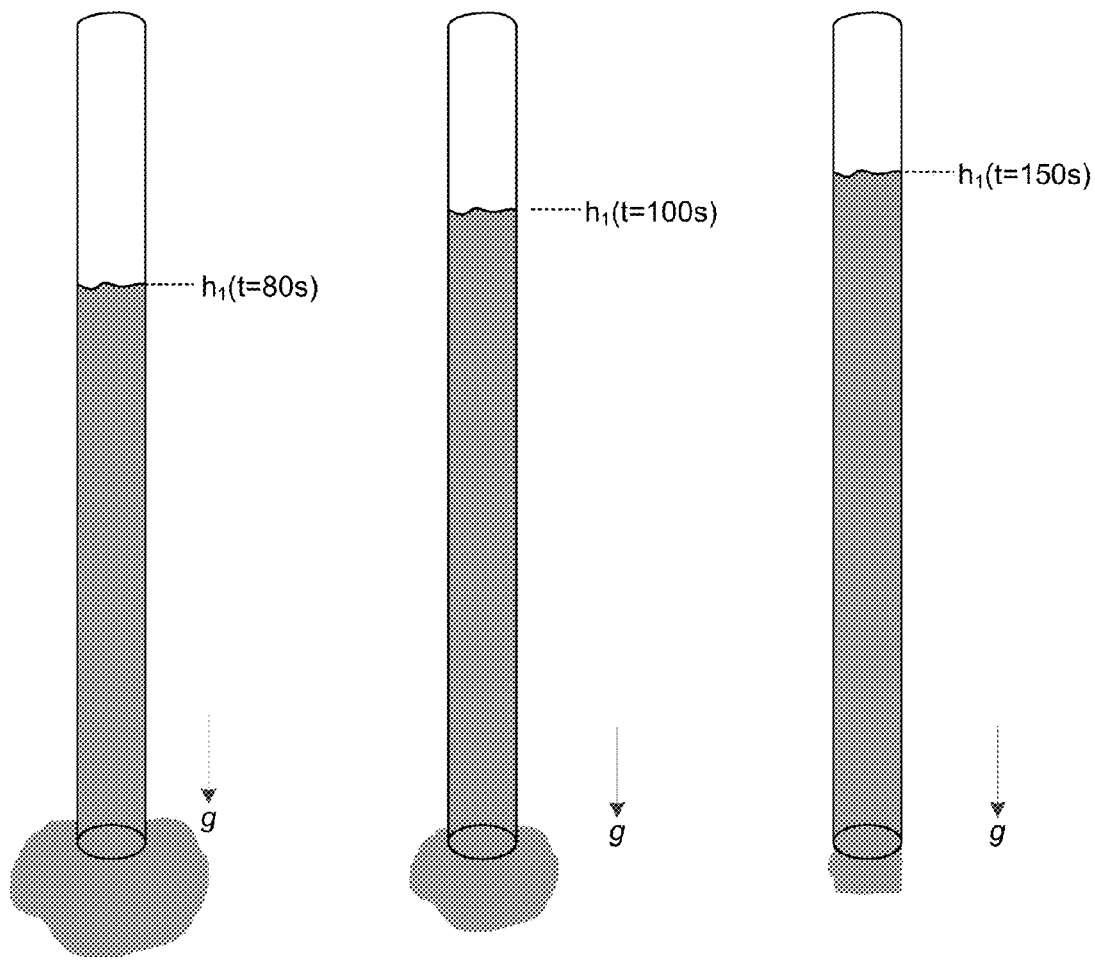
FIGS. 9A-9C illustrate an example implementation of a wellbore fluid filling a conduit.

In step 802, a computing system receives one or more images of a wellbore fluid sample that at least partially fills a vertically-orientated conduit. For example, the computer 205, and specifically the fluid property engine 255, receives the one or more images of a wellbore fluid filling a vertically-orientated conduit (e.g., vertically-orientated with respect to gravity g). As shown in FIGS. 9A-9C, a wellbore fluid 902, similar to the wellbore fluid 402, fills a conduit 904, similar to the wellbore fluid 404. Specifically, the conduit 904 is positioned adjacent a "pool" of the wellbore fluid 902 (e.g., the conduct 904 is positioned to touch or be in contact with a "puddle" of the wellbore fluid 802) such that the wellbore fluid 902 fills the vertically-orientated conduit 904, as shown in FIGS. 9A-9C. In some examples, each of the FIGS. 9A-9C can correspond or be associated with the one or more images of the wellbore fluid 902 filling the conduit 904. In some examples, the one or more images of the wellbore fluid 902 filling the conduit 904 can include multiple (e.g., two or more) images of the wellbore fluid 402 filling the conduit 404 (e.g., a sequence of multiple still images, or a video). In some examples, the wellbore fluid 902 fills the conduit 904 via capillary action.

In some examples, the wellbore fluid 902 is a fracturing fluid (e.g., the fluid 162). In some examples, the conduit 904 is a capillary tube. In some examples, the wellbore fluid 902 is a non-Newtonian fluid. In some examples, the wellbore fluid 902 is a Newtonian fluid.

In step 804, a computing system determines a steady-state level of the wellbore fluid sample within the conduit based on the one or more images. For example, the computer 205, and specifically the fluid property engine 255, determines the steady-state level of the wellbore fluid 902 within the conduit 904 based on the one or more images. Specifically, the fluid property engine 255 determines the height of the wellbore fluid 902 filling the conduit 904 for each of the one or more images. For example, each of the FIGS. 9A-9C depicts the wellbore fluid 902 filling the conduit 904 to certain heights at specific times, such that height of the wellbore fluid 902 filling the conduit 905 is a function of (or based on) the time. For example, FIG. 9A depicts the wellbore fluid 902 filling the conduit 904 to a height h(t=90 s) at 90 seconds; FIG. 9B depicts the wellbore fluid 902 filling the conduit 904 to a height h(t=100 s) at 100 seconds; and FIG. 9C depicts the wellbore fluid 902 filling the conduit 904 to a height h(t=150 s) at 150 seconds.

The computer, and specifically the fluid property engine 255, then determines a difference in height of the wellbore fluid 902 filling the conduit 904 across the one or more images (e.g., FIGS. 9A-9C). Specifically, the fluid property engine 255 compares the heights (e.g., h(t=90 s), h(t=100 s), h(t=150 s)) across the one or more images (FIGS. 9A-9C) to determine the difference (e.g., variation) between the heights of the wellbore fluid 902 within the conduit 904 of the one or more images. The fluid property engine 255 can identify whether the difference in height (e.g. variation) for the wellbore fluid 902 within the conduit 904 of the one or more images is within a predetermined tolerance. When the fluid property engine 255 identifies that the difference in height of the wellbore fluid 902 within the conduit 904 of the one or more images is within a predetermined tolerance, the fluid property engine 255 determines that the wellbore fluid 902 (and specifically, the height of the wellbore fluid 902) within the conduit 902 is in a steady-state level.

Figure 10:
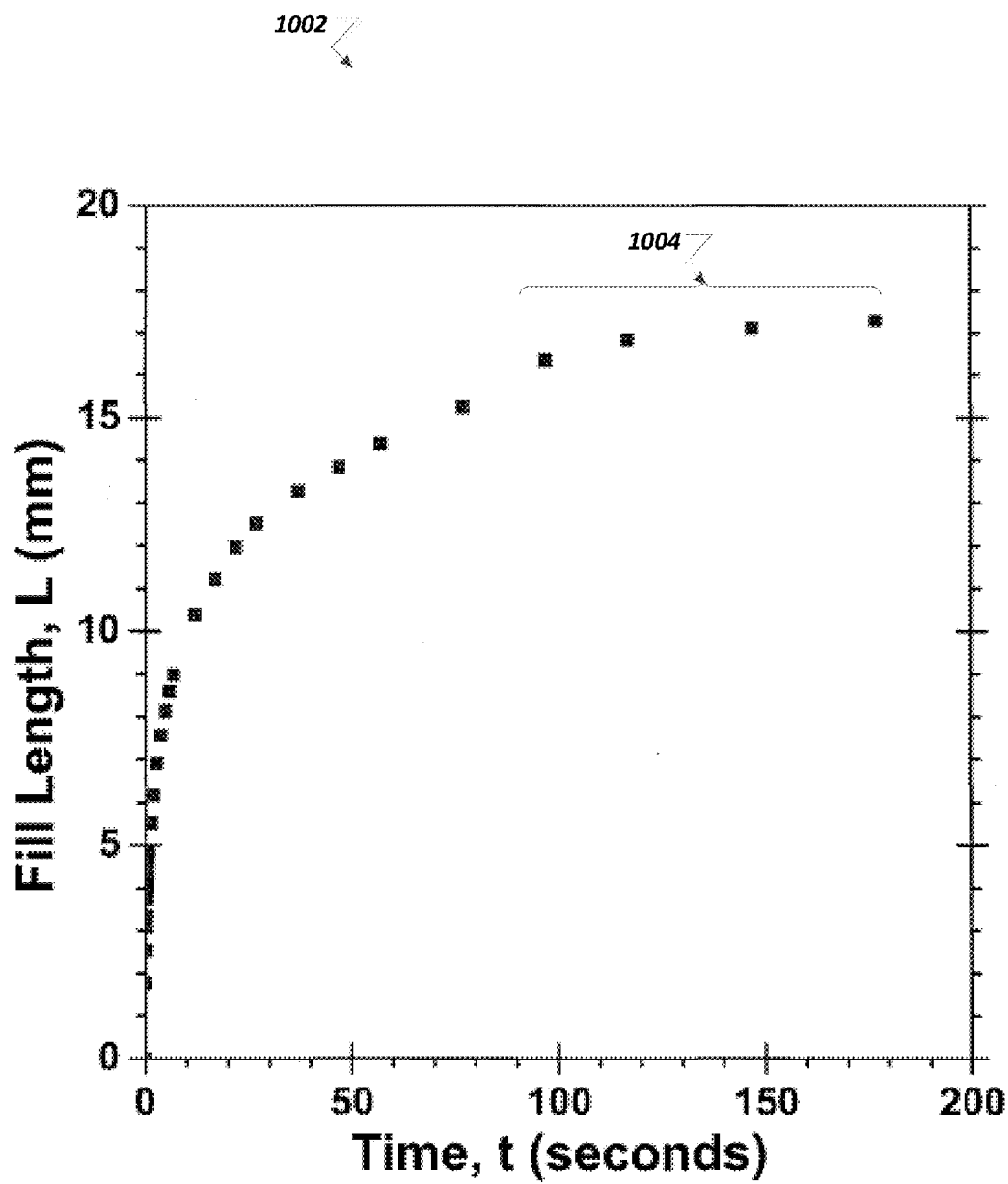
FIG. 10 illustrates a graph of a height of a wellbore fluid filling a conduit as a function of time.

FIG. 10 depicts a graph 1002 of the height of the wellbore fluid 902 filling the conduit 904 as a function of time. The graph 1002 includes one or more plot points graphically depicting that the variation in the height of the wellbore fluid 902 filling the conduit 904 decreases for each time point as the time of the wellbore fluid 902 filling the conduit 904 increase. Specifically, region 1004 indicates that the height of the wellbore fluid 902 has reached the steady-state level.

In step 806, the computing system determines a time duration to fill the conduit with the wellbore fluid sample to the steady state-level based on the one or more images. For example, the computer 205, and specifically the fluid property engine 255, determines the time duration for the wellbore fluid 902 to fill the conduit 904 to the steady-state level based on the one or more images (e.g., FIGS. 9A-9C). Specifically, after determining the steady-state level of the wellbore fluid 902 within the conduit 904, that is, the steady-state height of the wellbore fluid 902 within the conduit 904, a time associated with the steady-state height of the wellbore fluid 902 within the conduit 904 is determined. For example, the fluid property engine 255 determines that the time of 150 seconds is the time associated with the steady-state height of the wellbore fluid 902 within the conduit 904.

In step 808, the computing system determines a property of the wellbore fluid based at least in part on the steady-state level (of the wellbore fluid) and the time duration (associated with the steady-state level). For example, the computer 205, and specifically the fluid property engine 255, determines the property of the wellbore fluid 902 based at least in part in the steady state level of the wellbore fluid 902 within the conduit 904 and the associated time duration. In some examples, the property includes a hydration percentage of the wellbore fluid 902. In some examples, the property includes a viscosity of the wellbore fluid 902.

In some examples, the computer 205, and specifically the fluid property engine 255, determines the viscosity of the wellbore fluid 902. In some examples, the viscosity of the wellbore fluid 902 is determined in at least part on a density of the wellbore fluid 902 and a dimension of the conduit 904. In some examples, the dimension of the conduit 404 can include one or more of a height of the conduit 904, a radius of the conduit 904, and a length of the conduit 904.

In some implementations, the viscosity of the wellbore fluid 902 is based on the equation:

$$\mu = \frac{\rho g R^2 t}{8} \left( \frac{h_{ss} - h(t)}{h^2(t)} \right)$$

where $\mu$ is the viscosity of the wellbore fluid 902, $\rho$ is a density of the wellbore fluid 902, g is gravitational acceleration, R is the inner radius of the conduit, h is a height of the conduit 904, r is a radius of the conduit 904, t is the time duration (e.g., associated with the steady state level), $h_{ss}$ is the steady state level (e.g., height), and h(t) is a height of the wellbore fluid 902 within the conduit 904 as a function of the time.

In step 810, a visual representation of the property of the wellbore fluid to be displayed on a graphical user interface of the computing system 205 is prepared. For example, the computer 205 prepares a visual representation of the property (e.g., graphical data or text based data) to be displayed on a graphical user interface of the computer 205. Specifically, the computer 205 can prepare the visual representation for display on a display device (e.g., a display of a smart phone or a tablet computing device) of the computer 205 (e.g., one of the peripheral devices 290).

In some implementations, the steps of receiving the images and determining the time durations are performed at a wellsite (e.g., proximate wellsite assembly 100).

Figure 11:
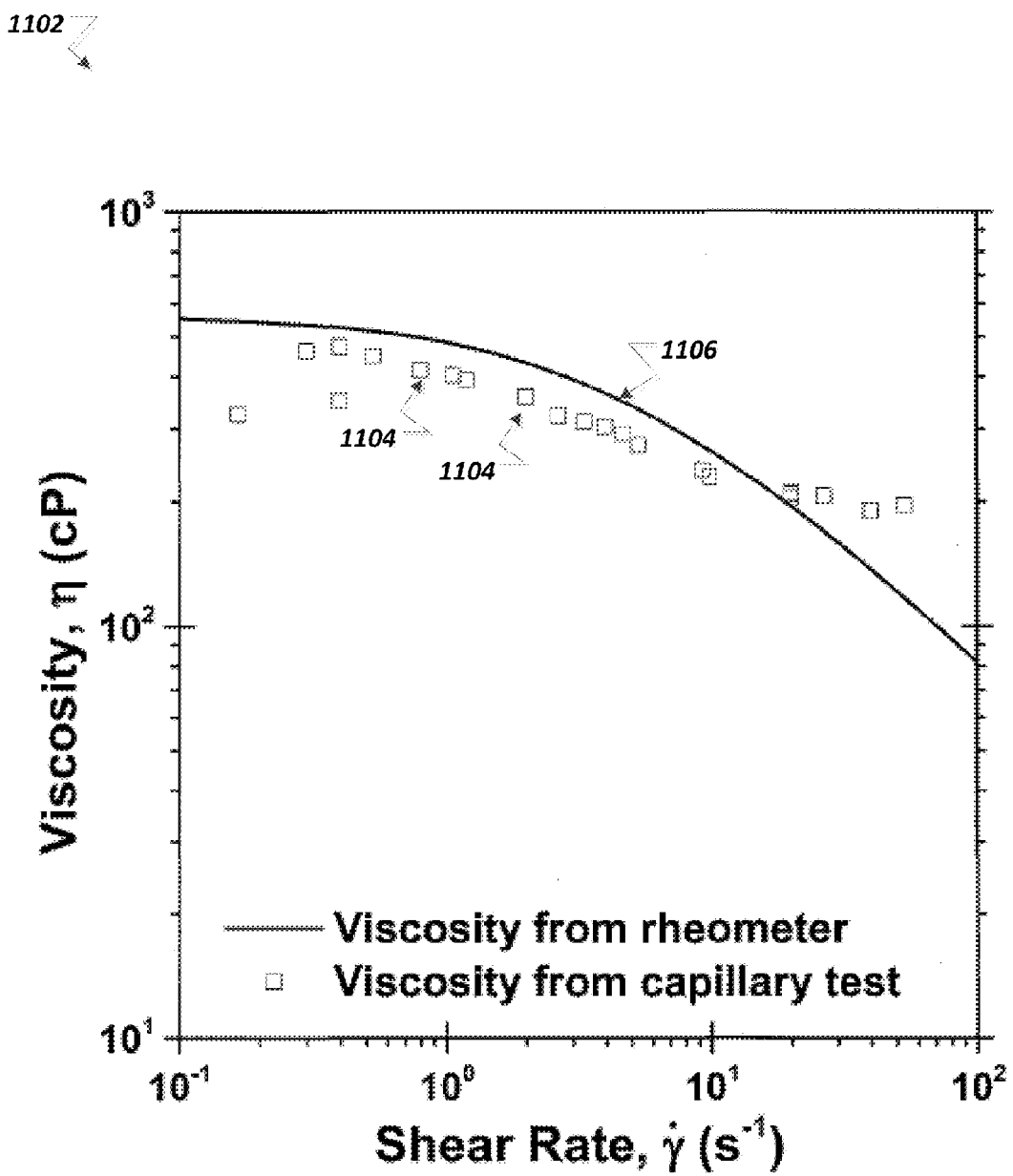
FIG. 11 illustrates a graph of a viscosity of a wellbore fluid filling a conduit as a function of shear rate.

An example of determining a property of the wellbore fluid 902 employing at least a portion of the method 800 of FIG. 8 is described herein. The vertically-orientated conduit 904, nominally 75 millimeters in length and 1.1 millimeters in bore diameter, is filled by a wellbore fluid 902 comprising 35-lb/1000 gal guar gum (mixed for 60-minutes on a blender). Images of filling of the conduit 904 by the wellbore fluid 902 were captured by a smart phone camera. The resulting filled height of the conduit 904 by the wellbore fluid 902 as a function of time is shown in FIG. 10. Additionally, a shear rate of the wellbore fluid 902 can be directly related to a velocity of the wellbore fluid 902 filling the conduit 904 and the diameter of the conduit 904. The viscosity of the wellbore fluid 902 can then be determined as a function of the shear rate of the wellbore fluid 902, as illustrated by graph 1102 in FIG. 11. Specifically, the viscosity profile (illustrated as multiple points 1104) of the wellbore fluid 902 can be determined from analysis of the one or more images (e.g., video) from the smart phone camera as the wellbore fluid 902 (35-lb/1000 gal guar gum) fills the conduit 904. As show in FIG. 11, this viscosity profile is shown in comparison with a similar curve 1106 that is determined in a traditional matter on a traditional rheometer at 75° F. using couette geometry. In this test, the steady-state height of the wellbore fluid 904 within the conduit 902 (e.g., $h_{ss}$) is 18.9 millimeters.

Figure 12:
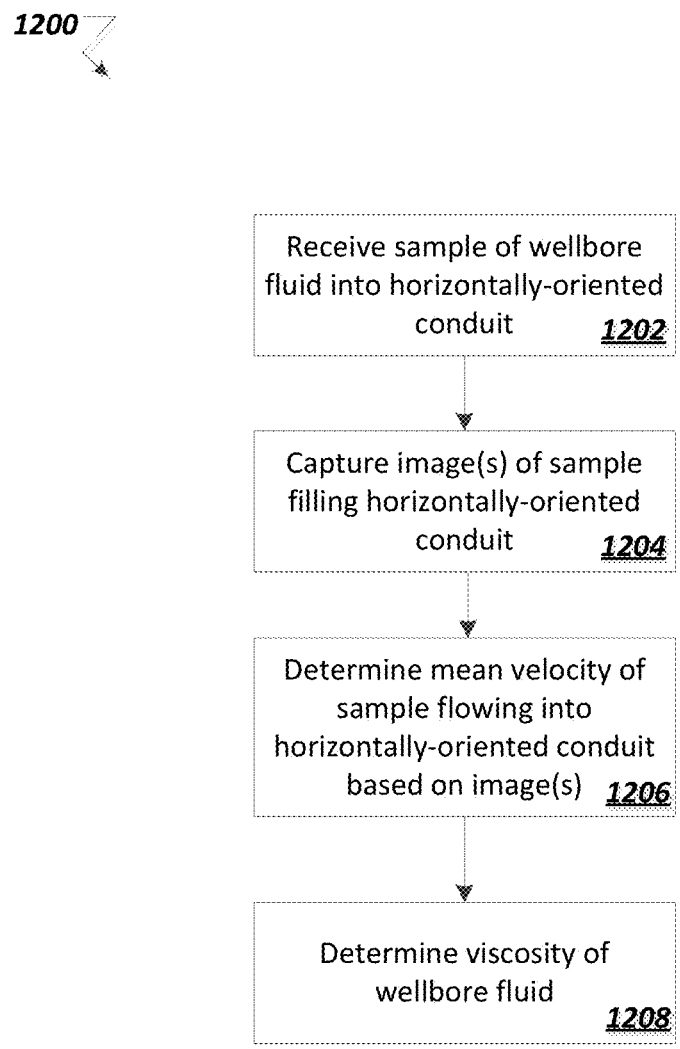
FIG. 12 illustrates an example method for determining a viscosity of a wellbore fluid.

FIG. 12 illustrates an example method 1200 for determining a viscosity of a wellbore fluid. For clarity of presentation, the description that follows generally describes method 1200 in the context of FIGS. 1 and 2. However, it will be understood that method 1200 may be performed, for example, by any other suitable system, environment, software, and hardware, or a combination of systems, environments, software, and hardware as appropriate. In some implementations, method 1200 may be used for determining viscosity of a wellbore fluid (e.g., a frac fluid) when a particular property of the wellbore fluid, such as a surface tension and/or conduit head height, $h_c$, of the wellbore fluid is known (e.g., from a database, historical data, or otherwise). Notably, method 1200 may be performed when exclusively using a horizontally-oriented (with respect to gravity) conduit, such as a capillary tube.

In step 1202, a sample of the wellbore fluid is puddled at an open end of a conduit (e.g., a capillary tube) that is horizontally-oriented with respect to gravitational acceleration. As shown in FIGS. 4A-4D, a wellbore fluid 402 (e.g., fluid 162) fills a conduit 404. Specifically, the conduit 404 is positioned adjacent a "pool" of the wellbore fluid 402 (e.g., the conduct 404 is positioned to touch or be in contact with a "puddle" of the wellbore fluid 402).

In step 1204, images are captured (e.g., by the computer 205 at the wellsite) of the sample filling the horizontally-oriented conduit. In some examples, each of the FIGS. 4A-4D can correspond or be associated with the image of the sample of the wellbore fluid 402 filling the conduit 404.

In step 1206, a mean velocity of the sample flowing into the horizontally-oriented conduit is determined (e.g., by the computer 205) based on the captured images. For example, the mean velocity may be determined by calculating a particular fill distance (e.g., length of conduit to which the sample fills the conduit) based on pixel length of conduit shown in the captured images relative to a time duration that it takes the sample to reach the particular fill distance.

In step 1208, the viscosity is determined based at least partially on the mean velocity of the sample and the known property of the wellbore fluid (e.g., surface tension and/or conduit head height, $h_c$). For example, in some implementations, the viscosity is determined according to the equation:

$$\mu = \frac{\rho g h_c R^2}{8LV}$$

where μ is the viscosity of the wellbore fluid, ρ is a known density of the wellbore fluid, g is gravitational acceleration, $h_c$ is a known property of capillary head height of the wellbore fluid, R is the inner radius of the conduit, L is a length of the conduit, and V is the mean velocity determined according to the captured image(s).

While operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the implementations described above should not be understood as requiring such separation in all implementations, and it should be understood that the described program components and systems can generally be integrated together in a single software product or packaged into multiple software products.

Particular implementations of the subject matter have been described. Other implementations, alterations, and permutations of the described implementations are within the scope of the following claims as will be apparent to those skilled in the art. For example, the actions recited in the claims can be performed in a different order and still achieve desirable results.

Accordingly, the above description of example implementations does not define or constrain this disclosure. Other changes, substitutions, and alterations are also possible without departing from the spirit and scope of this disclosure.

What is claimed is:

1. A computer-implemented method of determining a property of a wellbore fluid, the method comprising:
    receiving, at a computing system, one or more images of a wellbore fluid sample that at least partially fills a vertically-oriented conduit;
    determining, with the computing system, a steady-state level of the wellbore fluid sample within the conduit based on the one or more images;
    determining, with the computing system, a time duration to fill the conduit with the wellbore fluid sample to the steady-state level based on the one or more images; and
    determining, with the computing system, the property of the wellbore fluid based at least in part on the steady-state level and the time duration;
    where the property comprises a viscosity of the wellbore fluid determined at least in part on a density of the wellbore fluid and a dimension of the conduit based on the equation:

$\mu = [(\rho \times g \times r^2 \times t)/8] \times [(h_{ss} - h(t)/h^2(t))]$;

where μ is the viscosity, ρ is a density of the wellbore fluid, g is gravitational acceleration, h is a height of the conduit, r is a radius of the conduit, t is the time duration, $h_{ss}$ is the steady state level, and h(t) is a height of the wellbore fluid as a function of the time.

2. The method of claim 1, where the wellbore fluid comprises one of a fracturing fluid, drilling fluid, completion fluid, or formation stimulation fluid.

3. The method of claim 1, where the conduit comprises a capillary tube.

4. The method of claim 1, where the computing system comprises a smart phone or a tablet computing device and the steps of receiving and determining are performed at a wellsite, the method further comprising capturing the one or more images of the wellbore fluid sample with the smart phone or tablet computing device at the wellsite.

5. The method of claim 1, further comprising preparing a visual representation of the property of the wellbore fluid to be displayed on a graphical user interface of the computing system.

6. The method of claim 1, where the wellbore fluid is a non-Newtonian fluid.

7. A computer program product for determining a property of a wellbore fluid, the computer program product comprising computer readable instructions embodied on tangible media that are operable when executed to perform operations comprising:
    receiving one or more images of a wellbore fluid sample that at least partially fills a vertically-oriented conduit;
    determining a steady-state level of the wellbore fluid sample within the conduit based on the one or more images;
    determining a time duration to fill the conduit with the wellbore fluid sample to the steady-state level based on the one or more images; and
    determining the property of the wellbore fluid based at least in part on the steady-state level and the time duration
    where the property comprises a viscosity of the wellbore fluid determined at least in part on a density of the wellbore fluid and a dimension of the conduit based on the equation:

$\mu = [(\rho \times g \times r^2 \times t)/8] \times [(h_{ss} - h(t)/h^2(t))]$;

where μ is the viscosity, ρ is a density of the wellbore fluid, g is gravitational acceleration, h is a height of the conduit, r is a radius of the conduit, t is the time duration, $h_{ss}$ is the steady state level, and h(t) is a height of the wellbore fluid as a function of the time.

8. The computer program product of claim 7, where the wellbore fluid is a fracturing fluid.

9. The computer program product of claim 7, where the conduit is a capillary tube.

10. The computer program product of claim 7, where the operations of receiving and determining are performed at a wellsite with a smart phone or tablet computing device.

11. The computer program product of claim 10, where the operations further comprise preparing a visual representation of the property of the wellbore fluid to be displayed on a graphical user interface of the smart phone or tablet computing device.

* * * * *